US012642942B1

(12) United States Patent
Hamdan

(10) Patent No.: US 12,642,942 B1
(45) Date of Patent: Jun. 2, 2026

(54) CONNECTING BLOCK AND COLOR-CODING SYSTEM FOR INTRAVENOUS TUBING AND MEDICAL LINES

(71) Applicant: Tamim Hamdan, Brentwood, TN (US)

(72) Inventor: Tamim Hamdan, Brentwood, TN (US)

( * ) Notice: Subject to any disclaimer, the term of this patent is extended or adjusted under 35 U.S.C. 154(b) by 0 days.

(21) Appl. No.: 19/033,470

(22) Filed: Jan. 21, 2025

(51) Int. Cl.
　*A61M 25/02* 　　(2006.01)
(52) U.S. Cl.
　CPC ....... *A61M 25/02* (2013.01); *A61M 2025/024* (2013.01); *A61M 2205/584* (2013.01); *A61M 2209/084* (2013.01)
(58) Field of Classification Search
　CPC .......... A61M 250/02; A61M 2025/024; A61M 2025/028; A61M 2205/584
　See application file for complete search history.

(56) References Cited

U.S. PATENT DOCUMENTS

| | | | |
|---|---|---|---|
| 4,639,980 | A | 2/1987 | Peterson |
| 4,971,271 | A | 11/1990 | Sularz |
| 5,224,674 | A | 7/1993 | Simons |
| 5,334,186 | A | 8/1994 | Alexander |
| 6,458,104 | B2 | 10/2002 | Gautsche et al. |
| 7,098,406 | B1 | 8/2006 | Hammonds |
| 8,679,065 | B2 | 3/2014 | Schuman et al. |
| 9,808,573 | B1 | 11/2017 | Dooley |
| 10,271,918 | B2 | 4/2019 | Chow et al. |

| | | | | |
|---|---|---|---|---|
| 11,007,349 | B2 | 5/2021 | Vera | |
| 11,027,057 | B2 | 6/2021 | Bone et al. | |
| 11,147,912 | B1 | 10/2021 | Campbell | |
| 11,439,804 | B1 | 9/2022 | Dill | |
| 11,690,951 | B1 | 7/2023 | Hartman et al. | |
| 11,826,537 | B2 | 11/2023 | Roddy et al. | |
| 11,883,612 | B2 | 1/2024 | Albertsen et al. | |
| 12,029,876 | B1 | 7/2024 | Garshong, Sr. | |
| 12,036,374 | B2 | 7/2024 | Jansson et al. | |
| 2005/0103949 | A1 | 5/2005 | Ross et al. | |
| 2006/0237597 | A1* | 10/2006 | D'Andria | F16L 3/223 248/51 |
| 2009/0019678 | A1 | 1/2009 | Taylor | |
| 2013/0053812 | A1* | 2/2013 | Lehmann | F16L 3/222 137/315.01 |
| 2014/0061421 | A1 | 3/2014 | Lane | |
| 2014/0252177 | A1 | 9/2014 | Vera | |

(Continued)

*Primary Examiner* — Deanna K Hall
(74) *Attorney, Agent, or Firm* — Law Office of Vincent LoTempio PLLC; Vincent G. LoTempio; Robert L. Cerasa

(57) ABSTRACT

A system for the securing, grouping, organizing, labeling, and identifying of intravenous tubing (IV) and medical lines in clinical or hospital settings. Connecting blocks are monolithic and have a female end and male end to allow for a quick connection, and disconnection, of multiple connecting blocks together. Such ease of connection facilitates a linear, organized arrangement of medical tubes and lines. Connecting blocks feature flexible hooks to accommodate lines of different sizes and easy replacement of medical lines. Notches on the hooks help secure medical lines to the connecting blocks. Connecting blocks may vary in color, allowing for organization and distinction between medical lines. The present disclosure addresses widespread issues in the medical field wherein disorganized lines create an environment ripe for medical error.

5 Claims, 9 Drawing Sheets

(56)     References Cited

U.S. PATENT DOCUMENTS

| | | | |
|---|---|---|---|
| 2014/0306070 A1 * | 10/2014 | Hartsock ............. | A61M 5/1418 |
| | | | 248/68.1 |
| 2015/0144746 A1 | 5/2015 | Stewart | |
| 2016/0114103 A1 | 4/2016 | Burke | |
| 2022/0022991 A1 | 1/2022 | Ballard et al. | |
| 2022/0160956 A1 | 5/2022 | Lau | |

* cited by examiner

300

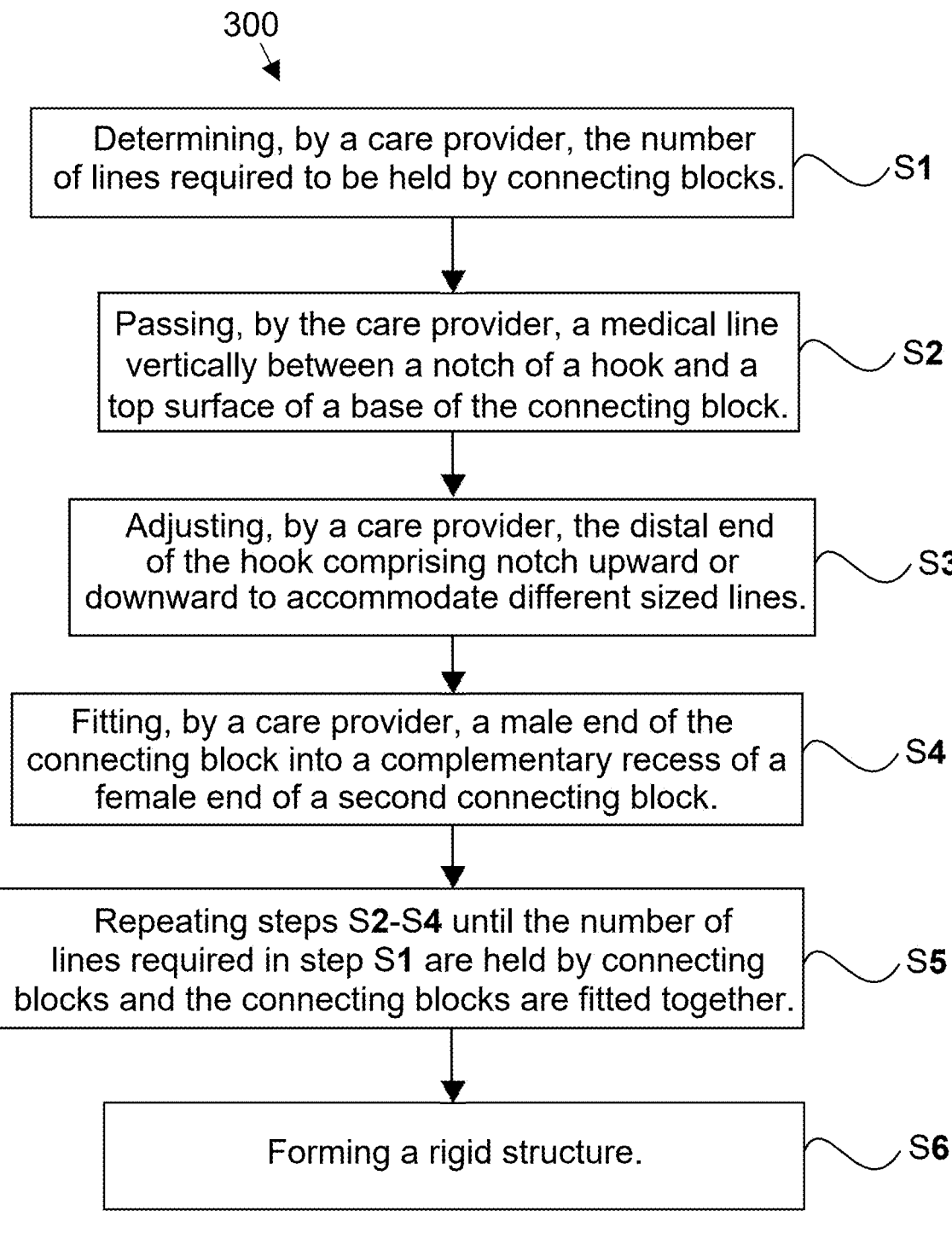

Determining, by a care provider, the number of lines required to be held by connecting blocks. — S1

Passing, by the care provider, a medical line vertically between a notch of a hook and a top surface of a base of the connecting block. — S2

Adjusting, by a care provider, the distal end of the hook comprising notch upward or downward to accommodate different sized lines. — S3

Fitting, by a care provider, a male end of the connecting block into a complementary recess of a female end of a second connecting block. — S4

Repeating steps S2-S4 until the number of lines required in step S1 are held by connecting blocks and the connecting blocks are fitted together. — S5

Forming a rigid structure. — S6

FIG. 8

CONNECTING BLOCK AND COLOR-CODING SYSTEM FOR INTRAVENOUS TUBING AND MEDICAL LINES

FIELD OF THE INVENTION

This disclosure relates to methods and apparatus for organizing intravenous tubing (IV) and medical lines in a hospital or clinical setting using one or more connecting blocks.

BACKGROUND

Intravenous (IV) tubing and medical lines, hereinafter "lines," are fundamental to patient care, enabling healthcare professionals to administer necessary medications, fluids, and treatments to a patient in a quick, efficient manner. Examples of medical lines include intravenous lines (IV), arterial lines (A-line), central venous catheters (CVC), naso-gastric (NG) tubes, gastrostomy tubes (G-Tube), jejunos-tomy tubes (J-Tube), chest tube (Thoracostomy Tube), uri-nary catheter (Foley Catheter), epidural catheter, hemodialysis catheter, swan-ganz catheter (Pulmonary Artery Catheter), peritoneal dialysis catheter, central lines, surgical drains, endotracheal tubes, and the like.

Lines are generally produced from soft plastics and are designed to carry fluids from one location to another, or from a source (i.e., medication or fluid bag) to a patient. Such lines and tubes are used extensively in medical settings. A 2023 report by Beecham and Tackling revealed that over 1 billion IV lines are used worldwide each year[1], with up to 80% of patients requiring peripheral IV access during a hospital stay.[2]

A patient can have multiple lines at a given time, even reaching as many as 15 lines. The tangling of such lines and tubes is common in health care and poses risks for care providers and patients. This tangling problem, coined "Spa-ghetti Syndrome" or "Infusion Confusion", has persisted in medicine with mentions in research as early as 1979. Despite this, the widespread problem remains ineffectively combat-ted. Recent studies have shown that hazardous tangles and errors relating to infusion are common and threaten patient well-being (Goodin et. al, 2012).[3]

Several aspects underlie the overall problem of line and tube management in medicine. First, lines show no indica-tion of their contents, and thus their identification and distinction require time and attentiveness. Failure to dis-tinctly identify lines may lead to dangerous, and potentially fatal, errors such as administering an incorrect treatment or overdosing. Additionally, a lack of distinction during one healthcare worker's shift can lead to compounding errors during subsequent healthcare workers' shifts.

Second, lines are inherently malleable and mobile leading to entanglement and confusion for medical staff. Addition-ally, entanglements can cause discomfort for patients and delay care in emergency situations.

Third, lines and tubing are changed often and for several reasons including medication administration, sanitation pur-poses, and changes in treatment regimens. Such a lack of distinction may lead to overlooked line maintenance given frequent interaction with lines, introducing added potential for errors.

Finally, in medicine, time is an exceptionally valuable resource and a difference of seconds in intervention can be a difference of life or death in patient outcomes. Elements within health care, like lines and their resulting challenges, diminish time in critical scenarios by demanding additional attention and engagement from care providers.

Thus, a heretofore unaddressed need exists in the industry to address the aforementioned deficiencies and inadequa-cies.

SUMMARY

The present disclosure generally relates to a connecting block and color-coding system for organizing intravenous tubing (IV) and medical lines, hereinafter "lines," in a hospital or clinical setting and method of using. While connecting blocks are designed to primarily accommodate intravenous tubing (IV) and medical lines, connecting blocks may facilitate organization of any wires, cords, lines, or leads used in a clinical setting. Examples include EKG leads and wires, temperature probe (thermistor probe) wires and leads, monitor wires and leads, and the like.

In accordance with the present disclosure, a monolithic connecting block, hereinafter "connecting block," is pro-vided comprising of a base, hook, female end, and male end. The female end defines a recessed shape for receiving the complementary protruding tab of a male end of a second connecting block. In one embodiment, the shapes of the male and female ends are triangular but may be of any complementary shape. Female and male ends on connecting blocks provide a means for an infinite amount of connecting blocks to be connected to one another depending on the number of lines requiring organization.

The present disclosure provides a connecting block to secure an intravenous tubing (IV) or medical lines to the connecting block by allowing the lines to pass vertically between the hook and top surface of the base. When a line passes between the hook and base, the hook may be flexed up or down to accommodate different sized lines. A line is fitted into a notch on the distal end of the hook. The connecting block does not need to be secured on a surface or to an individual in order to perform its described func-tions. For example, connecting block(s) may lay on the lines.

Connecting blocks may be color-coded for clearer dis-tinction among lines. The varying colors allow for labeling via color-coding. Connecting block colors are assigned to indicate specific line contents or applications. Connecting block colors can be used to standardize color-coded line and tube management across users, rooms, teams, units, or entire facilities and organizations. This tube management is espe-cially beneficial for instances where lines for differing purposes are required for patients or within a department or facility. However, it's important to note that color-coding connecting blocks is not mandatory for their use in line management. Other methods for distinguishing connecting blocks from one another include applying distinct stickers to the connecting blocks and/or marking connecting blocks with a writing instrument.

By using individual connecting blocks of varying colors connected together, a large, rigid structure is created unique to the lines they hold. The present disclosure combines three especially important functions including versatile color-based labeling of individual lines, the ability to create a customized, single rigid structure using several individual connecting blocks to secure and organize multiple lines, and adaptability of the resulting structure aligning with the unstable nature of medicine and treatment (i.e., connecting blocks be easily added, removed, and interchanged without impacting other lines).

Other systems, devices, methods, features, and advan-tages will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

The present invention and the manner in which it may be practiced is further illustrated with reference to the accompanying drawings wherein:

FIG. 8 illustrates an example of a flowchart of a method for holding a plurality of medical lines, according to an embodiment of the present disclosure.

DETAILED DESCRIPTION OF THE EMBODIMENTS

Figure 1:
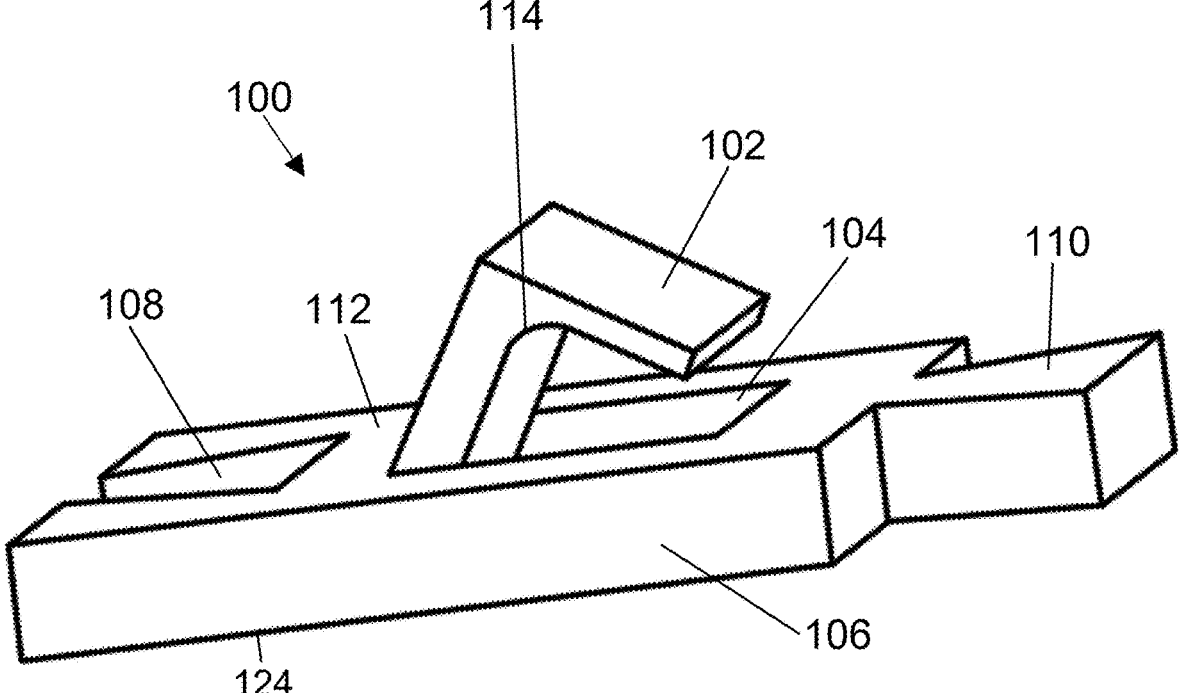
FIG. 1 is a side view of the connecting block, according to one embodiment of the present disclosure.

Reference is now made in detail to the description of the embodiments as illustrated in the drawings. While several embodiments are described in the connection with these drawings, there is no intent to limit the disclosure to the embodiment or embodiments disclosed herein. On the contrary, the intent is to cover all alternatives, modifications, and equivalents.

It should be clearly understood that like reference numerals are intended to identify the same structural elements, portions, or surfaces consistently throughout the several drawing figures, as may be further described or explained by the entire written specification of which this detailed description is an integral part. The drawings are intended to be read together with the specification and are to be construed as a portion of the entire "written description" of this invention as required by 35 U.S.C. § 112.

Referring now to the drawings, with reference to FIG. 1, a preferred embodiment of the present disclosure is depicted with connecting block 100. Connecting block 100 comprises a hook 102, base 106, female end 108, and male end 110. In a preferred embodiment, connecting block 100 is one monolithic piece molded from a plastic material but may be composed of other materials as well including, but not limited to, metals or polymers.

Base 106 comprises a top surface 112, bottom surface 124, and opposing lateral sides between the top and bottom sides as well as an aperture 104 through the top and bottom of the base 106.

Female end 108 defines a recess on a lateral end of the base 106 and male end 110 defines a protruding tab on an opposing lateral end of the base 106. The recess of the female end 108 is complementary in shape to the tab of the male end 110. In a preferred embodiment, male end 110 and female end 108 are trapezoidal in shape however any complementary shape may be used.

Multiple connecting blocks 100 may be coupled together by inserting the male end 110 into the female end 108 of an additional connecting block 100. Given connecting blocks 100 have both a female end 108 and male end 110, a limitless number of connecting blocks 100 may be connected together depending on personal need.

Hook 102 protrudes perpendicularly from the top surface 112 of base 106, having a proximal end molded to the top surface 112 and a distal end comprising a notch 114 for holding a line 200. Hook 102 is molded to the top surface 112 on the proximal end of the hook 102 and may be flexed up or down to accommodate different sized lines 200. The flexibility of hook 102 is based on the resiliency of the connecting block 100 material to allow for movement. Hook 102 serves as a clip, ensuring line 200 remains secure to the connecting block 100 by fitting line 200 between the notch 114 at a distal end of the hook 102 and the top surface 112 of the base 106.

In a preferred embodiment, notch 114 is semi-circular but may be V-shaped, U-shaped, and the like to accommodate different lines 200. When line 200 is fitted between the hook 102 and top surface 112 of the base 106, line 200 is fitted into the notch 114 and secured in place.

Figures 2A, 2B:
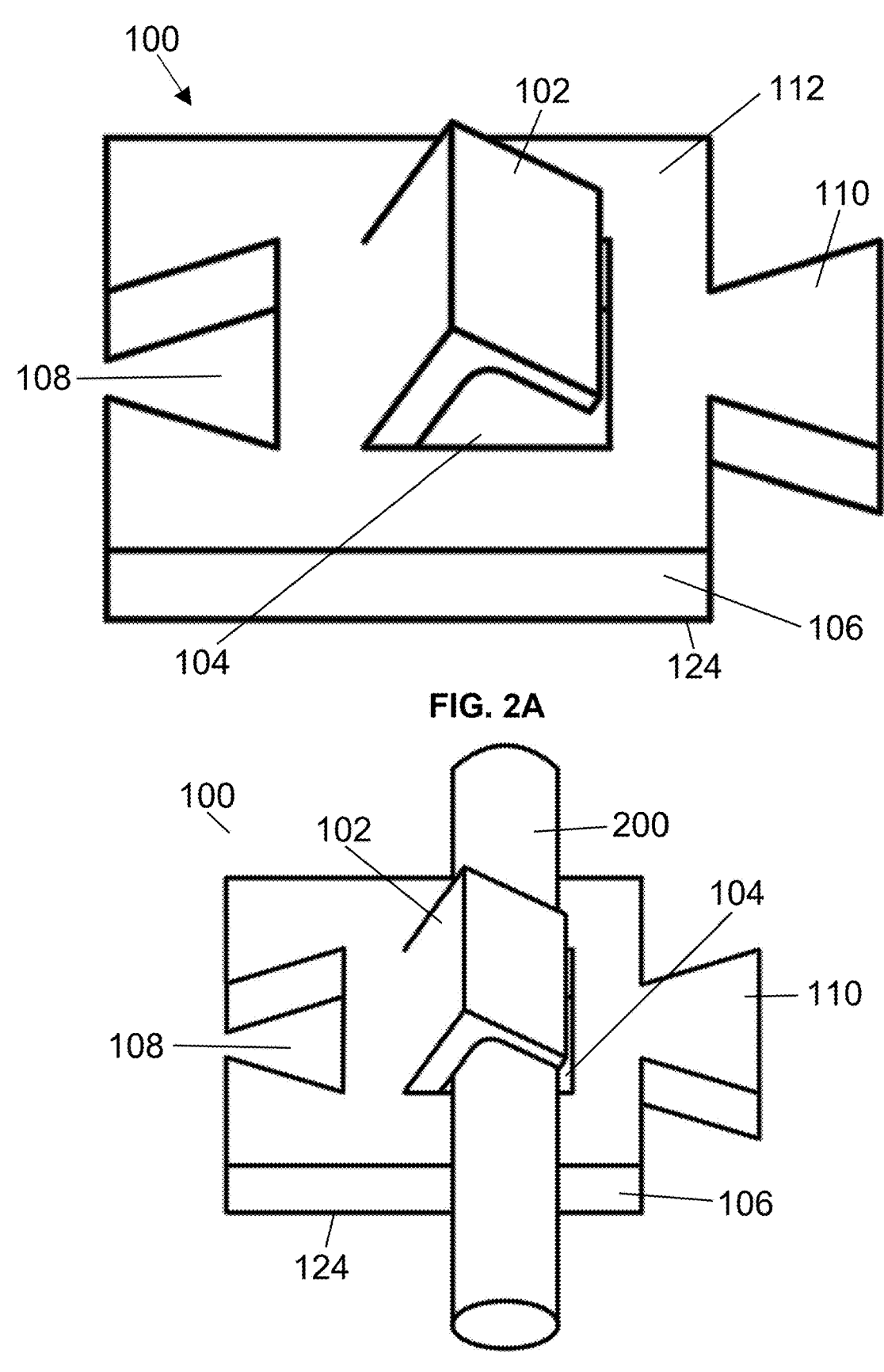
FIG. 2A is a perspective view of the connecting block, according to one embodiment of the present disclosure.
FIG. 2B is a perspective view of the connecting block which includes tubing, according to one embodiment of the present disclosure.

Referring now to FIGS. 2A and 2B, a preferred disclosure is depicted with connecting block 100. FIG. 2A illustrates a preferred embodiment of the connecting block 100 wherein aperture 104 is illustrated through the top surface 112 and bottom surface 124 of the base 106. Female end 108 and male end 110 are shown as complementary shapes whereby male end 110 may be fitted into the female end 108. FIG. 2B illustrates a line 200 vertically positioned in the notch 114 of the hook 102 and across the top surface 112 of the base 106. Hook 102 may be flexed up or down to accommodate different sized lines 200.

Connecting blocks 100 may be secured anywhere on a line 200 according to care provider preference. Care provider preferences may include visibility of the connecting block or accessibility. In a preferred embodiment, connecting block 100 is positioned on the central portion of a line 200, somewhere between where the line 200 starts and a patient.

Figure 3A:
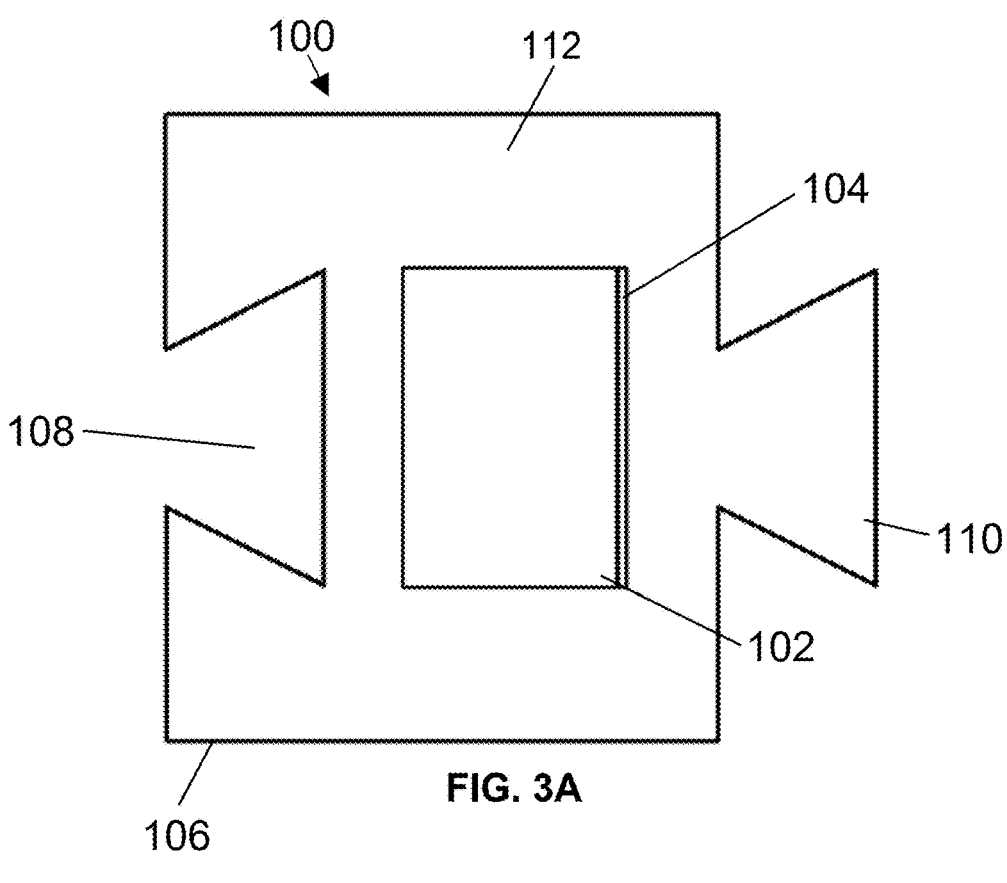
FIG. 3A is a top view of the connecting block, according to one embodiment of the present disclosure.
Figure 3B:
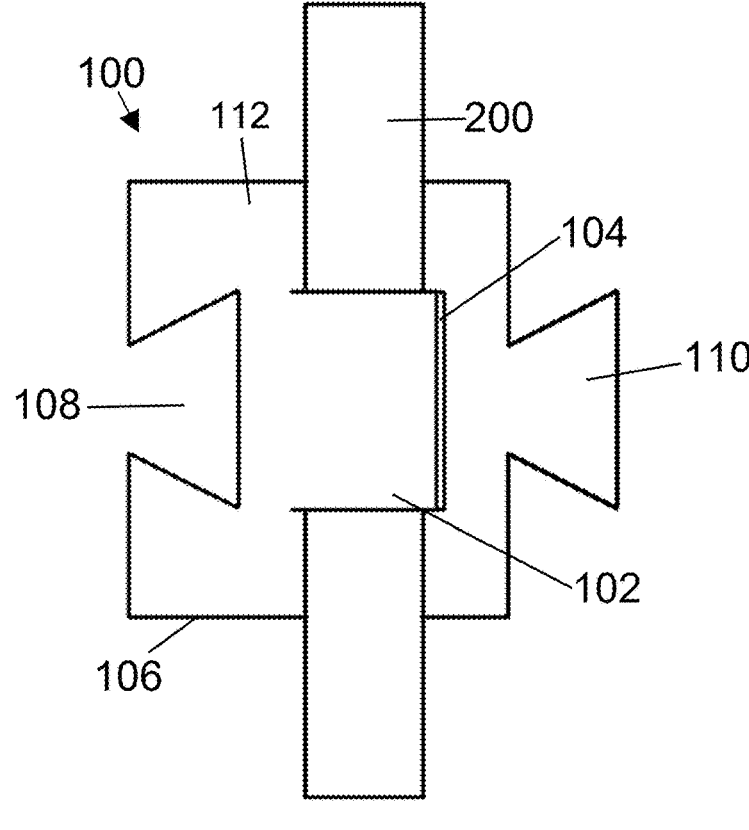
FIG. 3B is a top view of the connecting block which includes tubing, according to one embodiment of the present disclosure.

FIG. 3A illustrates a top view of the connecting block 100 and FIG. 3B illustrates a top view of the connecting block 100 holding a line 200. In FIG. 3A and FIG. 3B, the complementary shapes of the female end 108 and male end 110 can be seen as well as the top surface 112 of base 106 and hook 102.

5

Figure 4A:
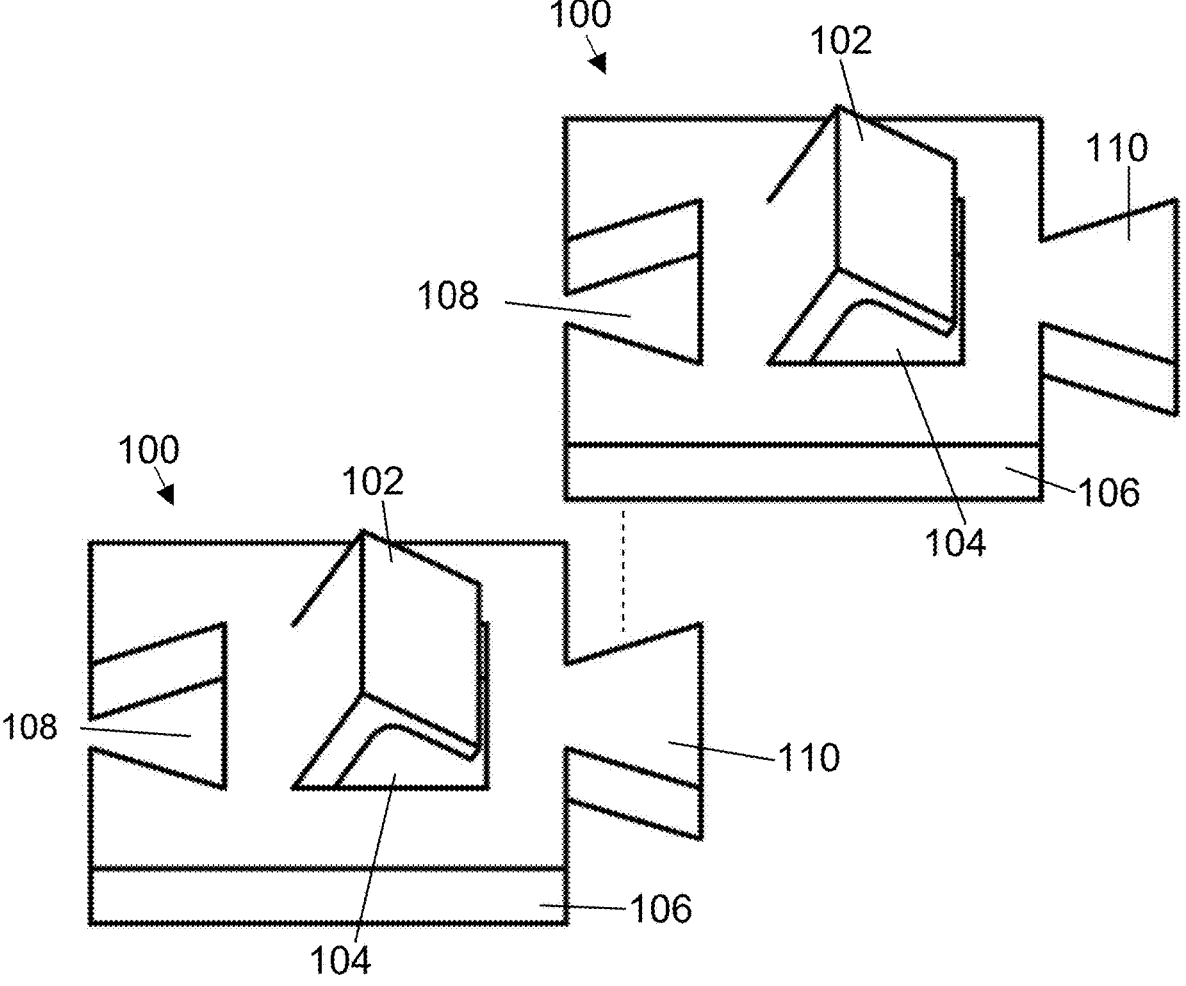
FIG. 4A illustrates a perspective view of connecting blocks being connected, according to one embodiment of the present disclosure.

FIG. 4A illustrates connecting blocks 100 being connected together according to one embodiment, whereby connecting blocks 100 are connected by fitting the female end 110 of one connecting block 100 over the male end 108 of a second connecting block 100. In other embodiments, male end 108 may be fitted into the female end 110 of a second connecting block. Attached connecting blocks 100 are designed to be separable, such that they can be disengaged from one another with minimal force, allowing for disassembly and reassembly of the connecting blocks 100.

Figure 4B:
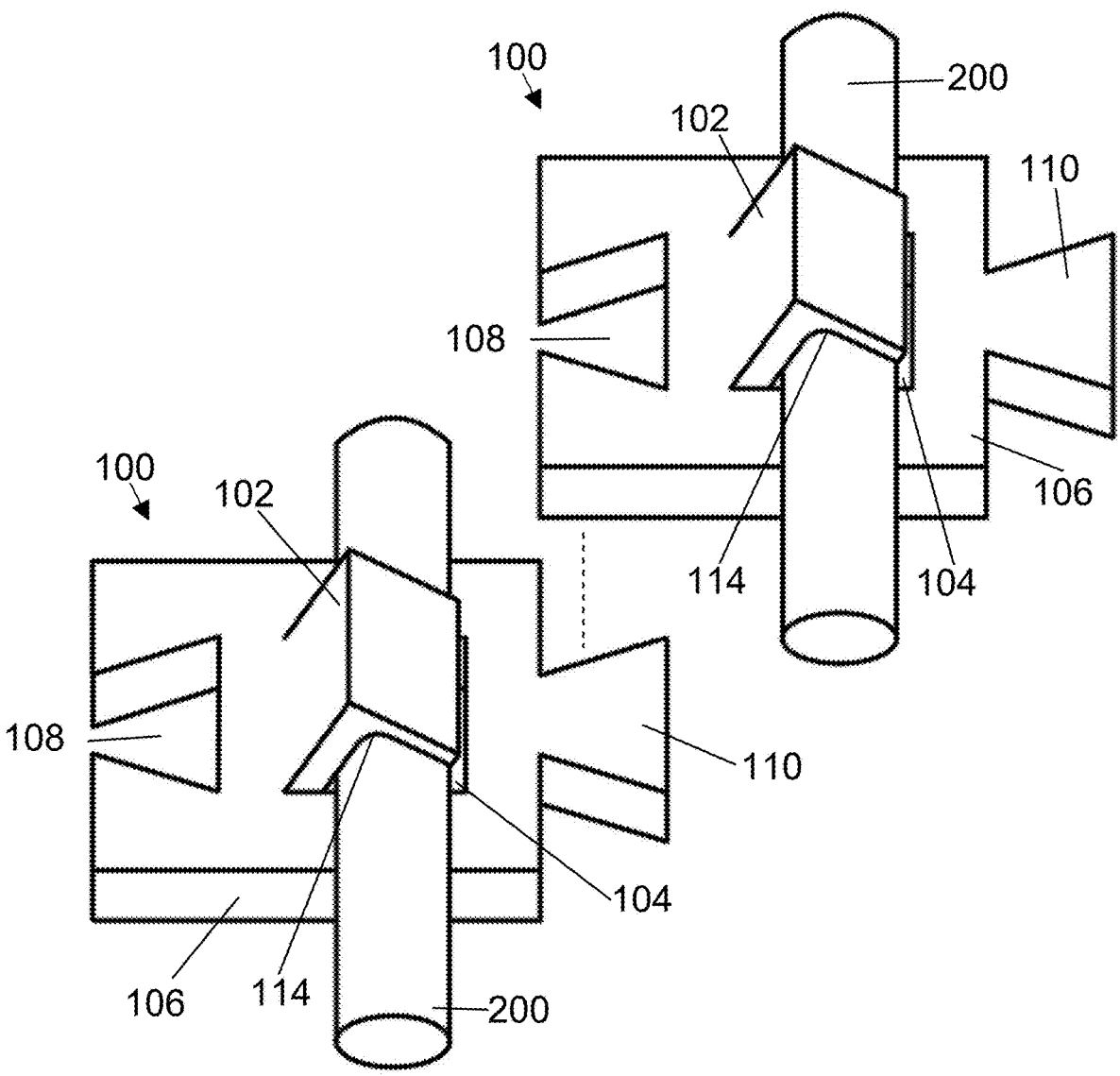
FIG. 4B illustrates a perspective view of lines secured to connecting blocks being connected, according to one embodiment of the present disclosure.

Furthermore, as illustrated by FIG. 4B, connecting blocks 100 may be connected, or disconnected, from one another while holding lines 200. Such ease of connections and disconnections enables a quick and efficient way of organizing lines 200 which can be critical in emergency situations. Additionally, this enables the reorganization of lines 200 and connecting blocks 100 in situations where lines 200 may need to be maintained or otherwise replaced.

Figures 5A, 5B:
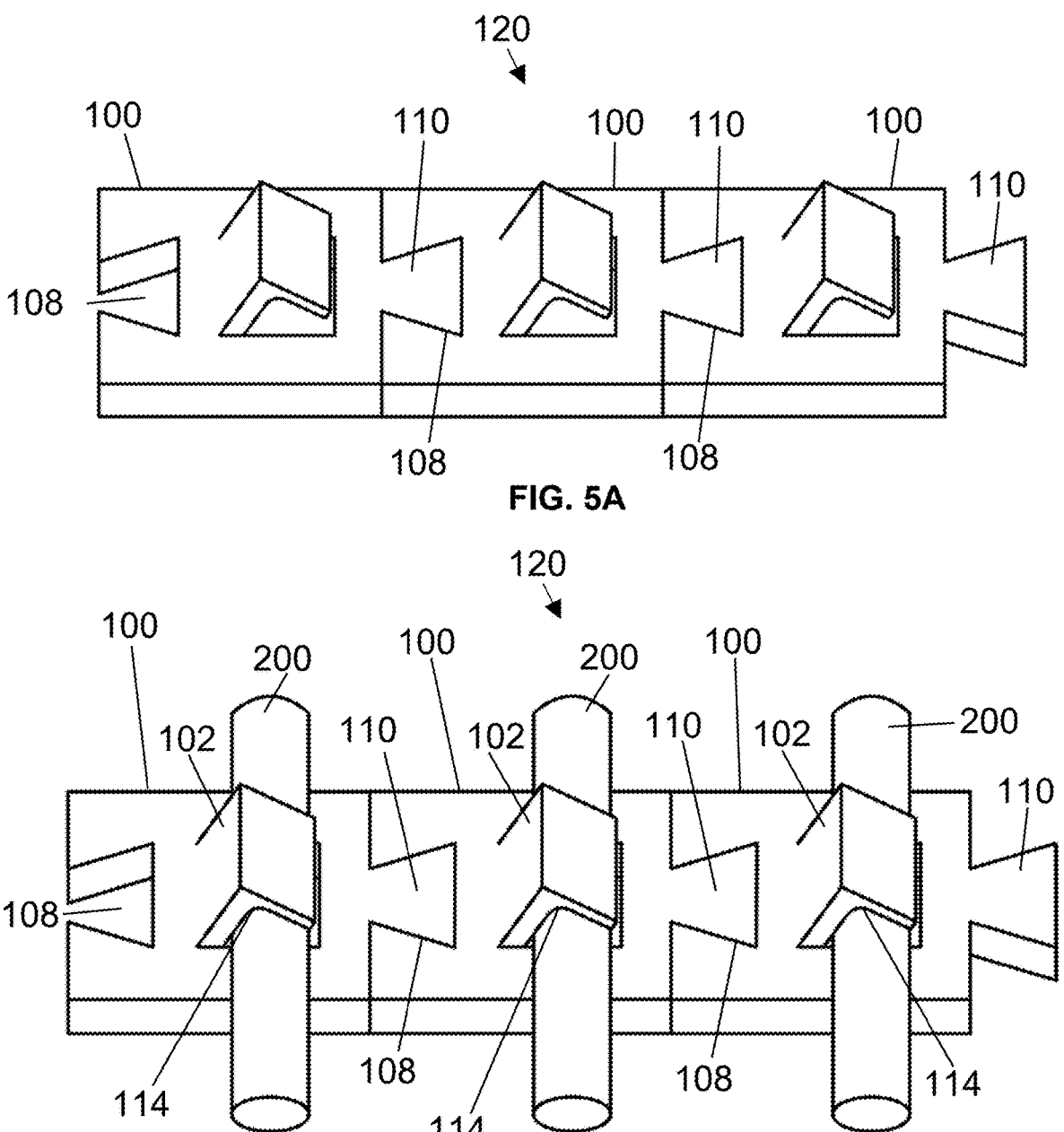
FIG. 5A illustrates a perspective view of connecting blocks of a rigid structure, according to one embodiment of the present disclosure.
FIG. 5B illustrates a perspective view of lines secured to connecting blocks of a rigid structure, according to one embodiment of the present disclosure.

FIG. 5A illustrates connecting blocks 100 connected together forming a rigid structure 120 according to one embodiment of the present disclosure. In this embodiment, male ends 110 connecting blocks 100 are fitted into the female ends 108 creating a rigid structure 120. Rigid structures 120 may be expanded by connecting additional connecting blocks 100 or reduced in size by eliminating connecting blocks 100 based on the number of lines 200 requiring organization by connecting blocks 100. FIG. 5B illustrates lines 200 being held between notch 114 of hooks 102 and top surface 112 of bases 106. Flexibility of hooks 102 allow for lines 200 to be replaced or removed from connecting blocks 100 while connecting blocks 100 are connected in a rigid structure 120 configuration.

Figure 6A:
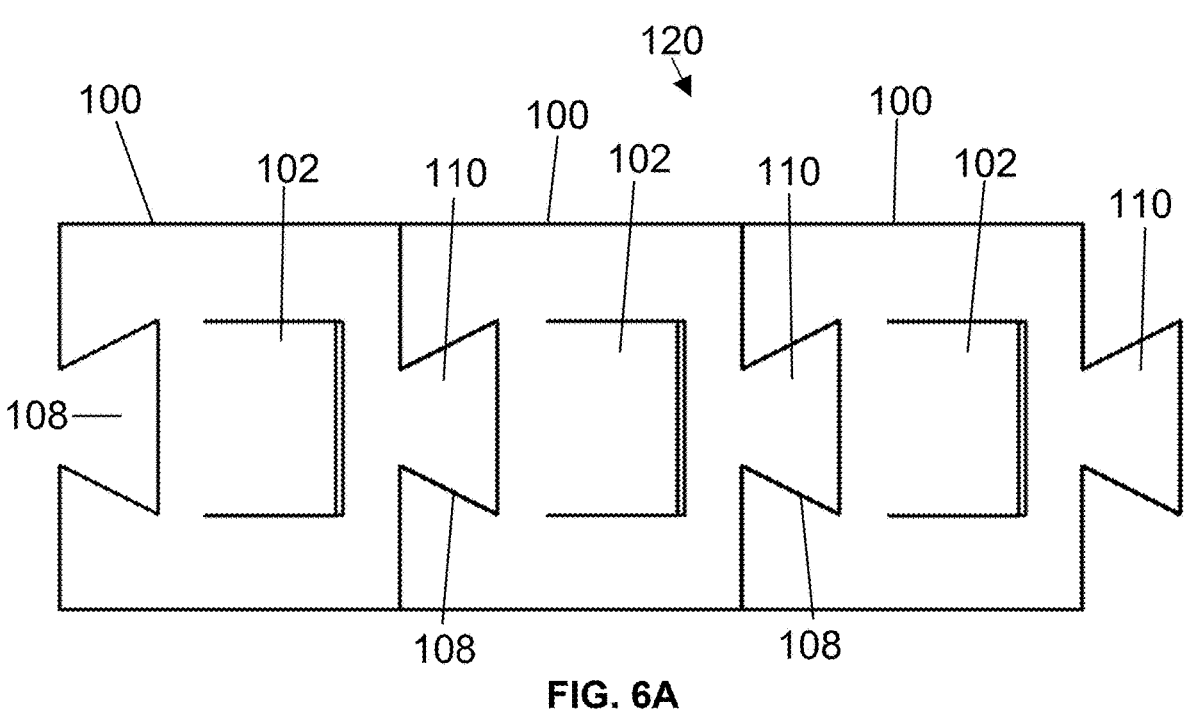
FIG. 6A illustrates a top view of connecting blocks of a rigid structure, according to one embodiment of the present disclosure.
Figure 6B:
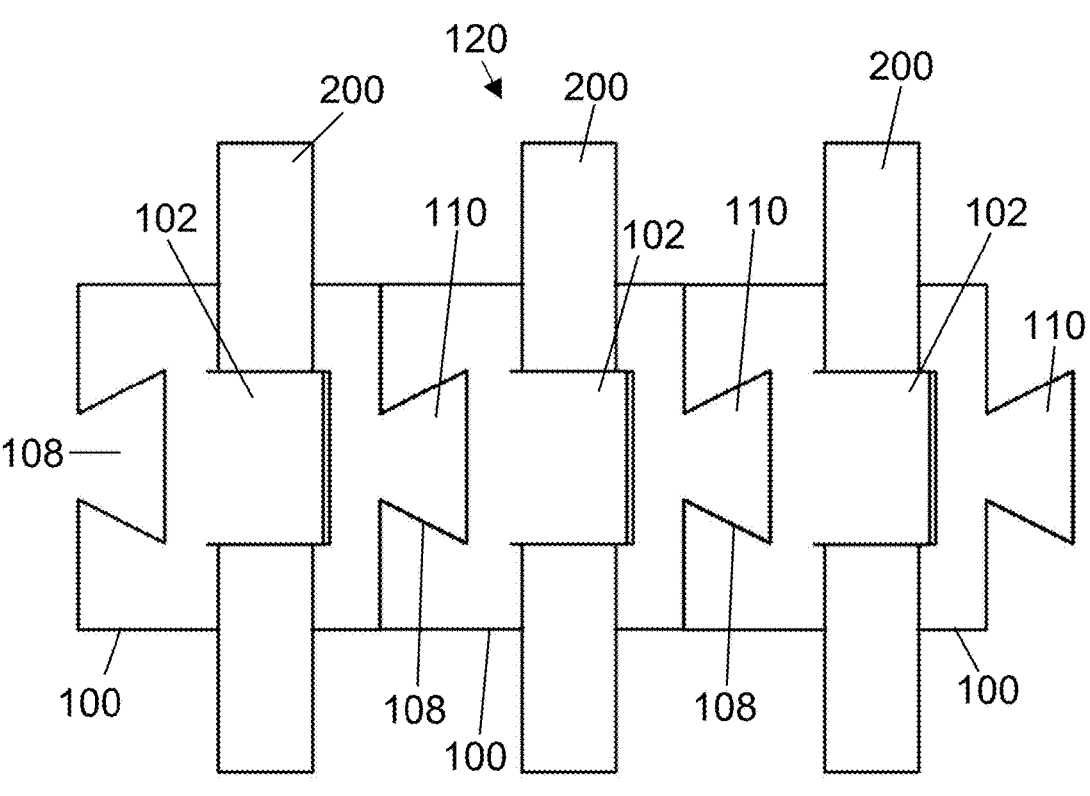
FIG. 6B a top view of lines secured to connecting blocks of a rigid structure, according to one embodiment of the present disclosure.

FIG. 6A illustrates a top view of the rigid structure 120 formed of multiple connecting blocks 100 and FIG. 6B illustrates a top view of the rigid structure 120 whereby lines 200 are held by connecting blocks 100.

Figure 7:
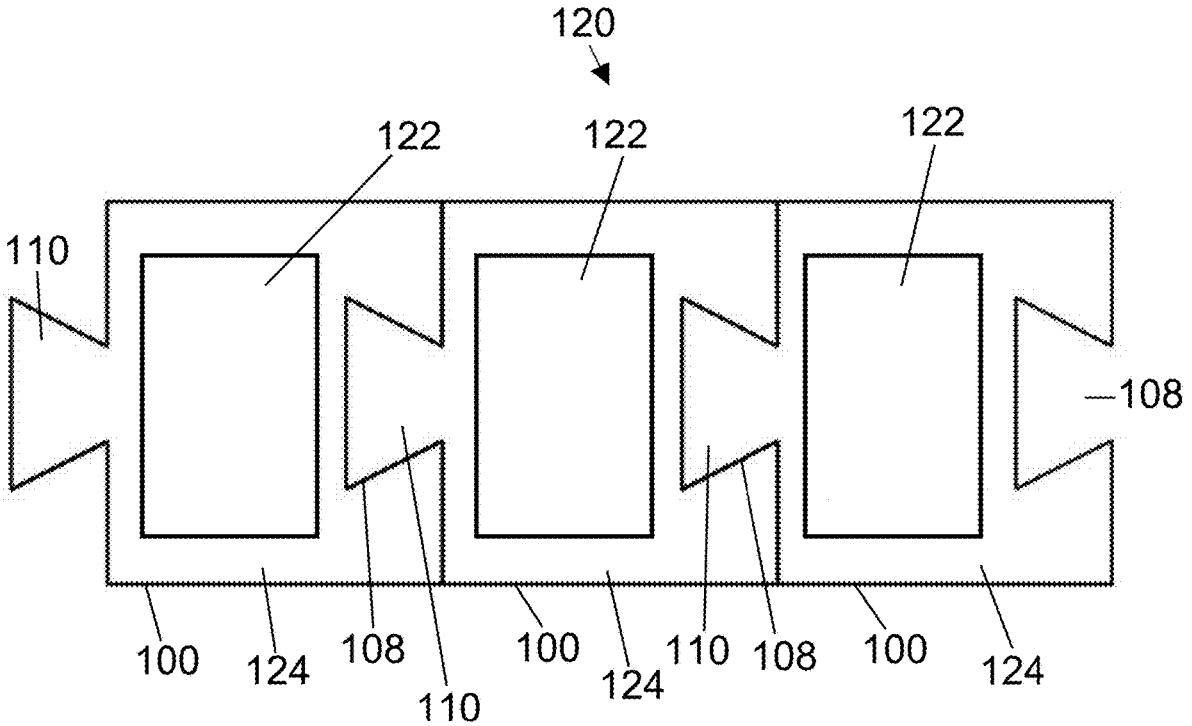
FIG. 7 illustrates a perspective view of an adhesive member attached to the underside of the connecting block, according to one embodiment of the present disclosure.

FIG. 7 illustrates an alternative embodiment of connecting block 100 having an adhesive member 122 on the bottom surface 124 for the purposes of mounting connecting block(s) 100 to a wall, machine, or other smooth surface. Adhesive member 122 having a first side securely, or removably, attached to the bottom surface 124 and a second side removably attached to a wall, machine, or other smooth surface. Adhesive member 122 may be of any shape with removable adhesive applied to the top surface and bottom surfaces of the adhesive member 122. Removable adhesives may include, for example, tapes, glues, magnets, and/or related adhesives for the purposes of temporary mounting use without leaving residue or damaging surfaces.

FIG. 8 illustrates an example of a flowchart of a method 300 for holding a plurality of lines 200. First, step S1 in which a care provider determines the number of lines 200 required to be held by connecting blocks 100. Thereafter, step S2 is performed in which line 200 is passed vertically between the notch 114 of hook 102 and base 106. In step S3, the distal end of the hook 102 comprising notch 114 may be adjusted upward or downward relative to the top surface 112 of the base 106 to accommodate different sized lines 200 thereby securing lines 200 to the connecting block 100 and preventing lines 200 from falling out of the connecting block 100. In step S4, male end 110 of the connecting block 100 is fitted into the complementary recess of female end 108 of a second connecting block 100. In step S5, steps S2-S4 are repeated until the determined number of lines 200 in step S1 are all secured to connecting blocks 100. Once all connecting blocks 100 required to hold lines 200 are fitted together, a rigid structure 120 is formed in step S6. Alternatively, connecting blocks 100 may be secured together after step S1, prior to passing and securing lines 200 to connecting blocks 100. In another embodiment, lines 200 may be secured to individual connecting blocks 100 first and then connecting blocks 100 are secured to one another as described in step S4.

In additional embodiments, the care provider may assign versatile color-based labeling of individual lines in order to standardize color-coded line and tube management across users, rooms, teams, units, or entire facilities and organization. Additionally, care providers may apply an adhesive member 122 to secure the block 100 to a wall, machine, or other smooth surface.

The term "care provider" as used herein refers to someone who administers medical lines or intravenous (IV) therapy to patients or works with related medical tubing in a medical setting including nurses, paramedics and EMTs, phlebotomists, infusion therapists, medical assistants, physicians, physician assistants, anesthesiologists, certified registered nurse anesthetists, respiratory therapists, radiologic technologists, dialysis technicians, surgical technicians, gastroenterologists, GI nurses, urologists, urology nurses, wound care specialists, home health aides, veterinarians, veterinary technicians, biomedical engineers, biomedical technicians, and the like.

Although exemplary embodiments have been shown and described, it will be clear to those of ordinary skill in the art that a number of changes, modifications, or alterations to the disclosure as described may be made. All such changes, modifications, and alterations should therefore be seen as within the scope of the disclosure.

REFERENCES

[1] Beecham, Gabriel B. and Gary Tackling. "Peripheral Line Placement." *StatPearls*, StatPearls Publishing, 25 Jul. 2023.
[2] Presley, Brad. and Jonathan D. Isenberg. "Ultrasound-Guided Intravenous Access." StatPearls, *StatPearls* Publishing, 25 Jul. 2023.
[3] Goodin, Heather Janiszewski, et al. "Pediatric Medical Line Safety: The Prevalence and Severity of Medical Line Entanglements." *Journal of Pediatric Nursing*, vol. 27, no. 6. December 2012. pp. 725-733.

What I claim is:

1. A system for organizing a series of medical lines comprising:

a series of connecting blocks to form a substantially linear rigid structure for securing the series of medical lines;

wherein each connecting block comprises a base having a top surface, a bottom surface, a female end defining a recess and a male end defining a tab to correspondingly fit to the shape of the female end for selective removable engagement with an adjacent connecting block;

a resiliently flexible hook protruding perpendicularly from the top surface of the base, the hook comprising a distal end having a notch;

wherein, upon insertion of a medical line between the notch and the top surface, the hook is resiliently displaced and returns to a nominal position to retain the medical line within a space defined between the notch and the top surface of the base; and wherein the base defines an aperture located vertically beneath the notch of the hook, the aperture creating a clearance space that prevents the medical line and any external components thereof from resting on the top surface of the base to alleviate pressure and prevent occlusion, and provides a window of visibility through the base.

2. The system of claim 1, wherein the recess of the female end is generally triangularly shaped to fit the tab of the male end.

3. The system of claim 1, wherein the connecting block is color-coded to identify the medical line it secures.

4. The system of claim 1, wherein the connecting block has a dual sided adhesive member attached to the bottom surface of the base for mounting to a surface.

5. The system of claim 4, wherein the surface is a wall, a machine, or flat surface.

\* \* \* \* \*